United States Patent [19]

Anderson et al.

[11] 4,041,953
[45] Aug. 16, 1977

[54] CARDIAC PACER CIRCUIT

[75] Inventors: Jon A. Anderson, Marine-on-the-St. Croix; Richard W. Kramp, Bloomington, both of Minn.

[73] Assignee: Cardiac Pacemakers, Inc., St. Paul, Minn.

[21] Appl. No.: 677,735

[22] Filed: Apr. 16, 1976

Related U.S. Application Data

[63] Continuation of Ser. No. 515,463, Oct. 17, 1974, abandoned, which is a continuation-in-part of Ser. No. 460,585, April 12, 1974, abandoned.

[51] Int. Cl.$^2$ .............................................. A61B 1/36
[52] U.S. Cl. ............................. 128/419 PG; 128/422
[58] Field of Search ................ 128/419 PG, 421, 422, 128/423

[56] References Cited

U.S. PATENT DOCUMENTS

| | | | |
|---|---|---|---|
| 3,345,990 | 10/1967 | Berkovits | 128/419 PG |
| 3,528,428 | 9/1970 | Berkovits | 128/419 PG |
| 3,547,127 | 12/1970 | Anderson | 128/419 PG |
| 3,661,157 | 5/1972 | Fyson et al. | 128/419 PG |
| 3,908,667 | 9/1975 | Bernstein | 128/419 PG |

Primary Examiner—William E. Kamm
Attorney, Agent, or Firm—Orrin M. Haugen

[57] ABSTRACT

A battery powered electronic circuit adapted for surgical implantation in the body of a patient suffering from intermittent heart block for providing electrical stimulation of the heart muscle upon detection of failure of normal heart activity. The circuit includes a pulse generator comprising an astable multivibrator which normally functions to produce a series of pulses of predetermined duration and at a predetermined repetition rate. The pulses are fed to a voltage doubler pulser which amplifies the pulses before they are applied through the output electrodes to the heart muscle. Also included in the system is an integrated circuit differential bandpass amplifier which is coupled to the output electrodes for amplifying the electrical output signal from the heart which is detected when ventricular contractions occur. The system further includes a level detector and a refractory one-shot multivibrator network. When the output from the amplifier occasioned by a natural heartbeat exceeds the threshold established by the level detector, the refractory one-shot multivibrator is triggered to produce a feedback control signal to the astable multivibrator and to the voltage doubler pulser circuit. The feedback control circuit resets the astable multivibrator and inhibits the voltage doubler pulser circuit from producing an artificial stimulating impulse.

4 Claims, 9 Drawing Figures

CARDIAC PACER CIRCUIT

CROSS-REFERENCE TO RELATED APPLICATIONS

This application is a continuation of application Ser. No. 515,463 now abandoned, filed Oct. 17, 1974 entitled "CARDIAC PACER CIRCUIT", which in turn is a Continuation-in-Part of application Ser. No. 460,585, filed Apr. 12, 1974 entitled "CARDIAC PACER CIRCUIT", now abandoned, and assigned to the same assignee as the present application.

BACKGROUND OF THE INVENTION

This invention relates generally to a cardiac pacer circuit and more specifically to an improved demand-inhibit cardiac pacer circuit for artificially stimulating the heart muscle only in the absence or interruption of normal heart activity.

Demand-inhibit pacers are known in the art. Typically, demand-inhibit pacers detect the electrical signal emitted from the heart characterizing the depolarization of the ventricular muscle tissue, commonly termed the R-wave signal. Upon an indication of an R-wave signal being delivered by the heart muscle, the inhibit function of the pacer becomes operative to inhibit delivery of an artificial stimulating pulse to the heart muscle as long as natural heartbeats are occurring at a prescribed rate. In other words, the inhibit function is operative for a single cycle only of the heart activity. Once having sensed the occurrence of an R-wave signal, the inhibit function prevents or precludes delivery of an artificial pulse until sufficient time has elapsed so that the next succeeding R-wave signal is due. One such system is disclosed in the Berkovits U.S. Pat. No. 3,345,990.

Demand-inhibit pacers have traditionally suffered from one serious deficiency. While the normal function of these devices is to inhibit the generation of an artificial stimulating pulse during periods of normal heart activity, the prior art demand-inhibit pacers have sometimes been unable to distinguish between the signal from a natural heartbeat and stray electrical noise which may be picked up by the implanted electrodes from external sources. In other words, prior art pacer devices, when subjected to external noise at certain frequency bands, may produce an inhibit signal to disable the generation and delivery of the artificial impulse. Should this happen at a time that normal heart activity has ceased, it could prove fatal to the patient.

This problem has been recognized, and approaches have been advanced for attempting to solve it. More specifically, in the Berkovits U.S. Pat. No. 3,528,428, there is disclosed a circuit which is capable of operating in two modes. In the absence of external noise, the circuit described in U.S. Pat. No. 3,528,428 operates to produce an inhibit signal for disabling the application of artificial stimulating pulses to the heart when normal heart activity is sensed. However, when external noise is detected by the system, the circuit shifts to a second and asynchronous mode of operation wherein artificial stimulating pulses are generated at a fixed, predetermined rate irrespective of normal heart activity. While the circuit just described provides a solution to the problem of insuring that external noise will not continuously inhibit the generation of heart stimulating signals, it does so at the expense of producing such heart stimulating signals even when they may not be required because of continuing normal heart activity.

SUMMARY OF THE INVENTION

In accordance with the aspects of the present invention, the demand-inhibit pacer circuit comprises six basic functional components, as follows:
1. An astable or free-running multivibrator;
2. A voltage doubler pulser;
3. An integrated circuit, high gain, differential, bandpass amplifier;
4. A level detector;
5. A refractory one-shot circuit; and
6. An inhibit/reset network.

The astable multivibrator operates in a conventional fashion to produce regularly occurring pulses which are applied to the voltage doubler pulser. The voltage doubler pulser amplifies the output from the multivibrator and applies them to the heart muscle by way of a pair of implanted electrodes, except upon the occurrence of a feedback control signal from the refractory one-shot. The electrical R-wave signal produced by the heart muscle is also picked up by the same electrodes and applied as an input to the integrated circuit amplifier. The output from the amplifier is connected to the level detector and only those signals which exceed a predetermined threshold will be capable of initiating operation of the refractory one-shot circuit to which the level detector is connected. The control signal from the refractory one-shot is first supplied via the reset/inhibit network to the voltage doubler pulser to inhibit application of a stimulating pulse to the electrodes. A predetermined time following the inhibiting of the stimulating pulse, the output from the refractory one-shot is coupled through the reset/inhibit network and is used to reset the astable multivibrator to an initial condition, and except during the high state of the output, otherwise irrespective of the state of its output at the time that the reset signal is generated. Thus, the system operates to cause the voltage doubler pulser to stimulate the heart except when the heart muscle itself is producing a natural R-wave signal of an amplitude and within the rate indicative of normal heart activity. In the event that the heart fails to produce such an R-wave signal within the proper time, there will be no output from the level detector to trigger the refractory one-shot, and, hence, no reset nor inhibit signal will be produced. As a result, the multivibrator will continue its cycle and will allow the voltage doubler pulser to generate a signal for artificially stimulating the heart.

In the implementation of the present invention, consideration has been given to the frequency characteristics of the normal R-wave electrical signal of the heart. The high gain, integrated circuit, differential, bandpass amplifier has been designed to pass only those signals having the requisite frequency characteristics so that the inhibit control signals will only be produced when normal heart activity is present.

The differential amplifier exhibits a high degree of rejection to differential continuous wave interference and to common mode continuous wave interference while still maintaining the demand type of operation. Since external noise, such as produced by frequently encountered normal 50-cycle, 60-cycle, or 400-cycle interference and the like, does not fall within the passband of the operational amplifier, the inhibit circuitry is essentially immune to such ordinary external noise. However, as a safeguard, the pacer circuit of this invention is also provided with a feature that permits it to operate in an asynchronous mode should it happen that the electrical noise picked up by the implanted electrodes is of a frequency falling within the bandpass amplifier's passband.

Accordingly, it is the principal object of the present invention to provide an improved demand-inhibit cardiac pacer circuit.

Another object of the invention is to provide a demand-inhibit type pacer which is highly immune to erratic operation which would otherwise be caused by exposure to common sources of external noise, but which switches to a fail-safe asynchronous mode in the presence of noise having the same frequency components as a normal heart depolarization signal.

Still another object of the invention is to provide an improved demand-inhibit cardiac pacer circuit which will continue its function in a normal mode irrespective of exposure to most common sources of external electrical noise.

Yet another object of the invention is to provide a demand-inhibit type cardiac pacer which is reliable in operation over extended periods of time.

A still further object of the invention is to provide an improved cardiac pacer of the demand-inhibit type which produces only modest current drain from its energy source.

Other and further objects of the present invention will become apparent to those skilled in the art upon a study of the following specification, appended claims, and accompanying drawings.

DESCRIPTION OF THE PREFERRED EMBODIMENT

Figure 1:
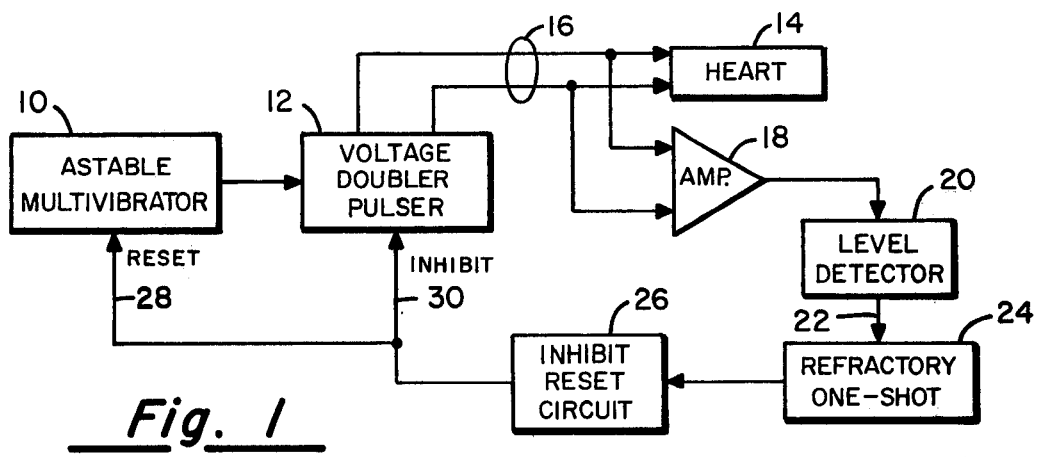
FIG. 1 is a block diagram illustrating the functional components of the preferred embodiment.

Referring first to FIG. 1 which illustrates a functional block diagram of the demand-inhibit pacer of the present invention, it can be seen that the system comprises a free-running or astable multivibrator 10 which normally functions to produce a series of pulses of a predetermined duration and at a desired repetition rate. For example, multivibrator 10 may be designed to produce pulses at a rate of 72 pulses per minute which corresponds at one pulse approximately every 833 milliseconds. The pulse amplitude may be in the range of from 1½ to 2½ volts.

The output from the astable multivibrator 10 is applied as an input to a voltage doubler pulser network 12 which serves to amplify the output from multivibrator 10 and to interface it with the load 14 (the heart) to which it is connected by means of the surgically implanted output electrodes 16. The resulting output pulse from the voltage doubler pulser may be in the range of 3½ to 5 volts in normal operation of the unit. The R-wave output from the heart muscle occurring during normal activity is sensed by the electrodes 16 and applied as an input to an operational amplifier 18. As will be more fully explained hereinbelow when the details of the schematic diagram are set forth, the amplifier 18 not only serves to amplify the R-wave signal but also acts as a bandpass filter such that only input signals of a predetermined frequency characteristic will be amplified and signals lying outside the passband will be attenuated. The output from amplifier 18 is connected to a level detector circuit 20 which functions to generate an output trigger signal on line 22 only when the R-wave signal picked up by electrodes 16 exceeds a predetermined threshold and has the prescribed normal frequency characteristic.

The signal on line 22 is used to initiate the refractory one-shot multivibrator network 24. Once initiated, the output from the refractory one-shot multivibrator network will revert from its stable state to its unstable state for a predetermined period and the resulting pulse output therefrom is applied to the inhibit/reset circuit 26 and from there by way of line 28 to the astable multivibrator 10 so as to reset the multivibrator to a reference state. Further, the output from network 26 is applied by way of line 30 to the voltage doubler pulser network 12 to inhibit any output therefrom. A time delay network in circuit 26 ensures that the inhibit operation occurs in advance of the reset operation.

In operation, the output from the astable multivibrator and voltage doubler pulser is applied by means of a pair of electrodes to the heart of a patient so as to effect ventricular stimulation. These electrodes are also used to pick up the naturally occurring electrical output from the heart when ventricular contractions occur. These signals received from the heart are amplified in the integrated circuit operational amplifier 18 and when the output thereof is of a sufficient amplitude and frequency characteristic so as to exceed the threshold established by the level detector 20 to thereby indicate a solid natural heartbeat, the level detector 20 produces a trigger signal to initiate operation of the refractory one-shot multivibrator network 24. Upon receipt of such a trigger signal, the one-shot circuit turns rapidly to its unstable state where it remains for a predetermined period before reverting to its normal standby stable state. The leading edge of the output signal from the refractory one-shot is used to perform two functions. First in time, it is applied to the voltage doubler pulser network 12 to inhibit the production of a pulse therefrom. Following this, it is fed back to the multivibrator network to initiate its switching cycle irrespective of its existing state at the time this reset signal is applied. Thus, the multivibrator causes the voltage doubler pulser to stimulate the heart except when an R-wave signal of a sufficient amplitude indicative of normal heart activity has been delivered by the heart. In the event that the heart fails to produce a natural R-wave signal at the proper time, there will be no output from the level detector 20 to trigger the refractory one-shot multivibrator network 24 and hence, neither a reset nor a inhibit signal will be produced. As a result, the multivibrator will continue its cycle and will allow the voltage doubler pulser 12 to generate a signal for artificially stimulating the heart.

Figure 2A:
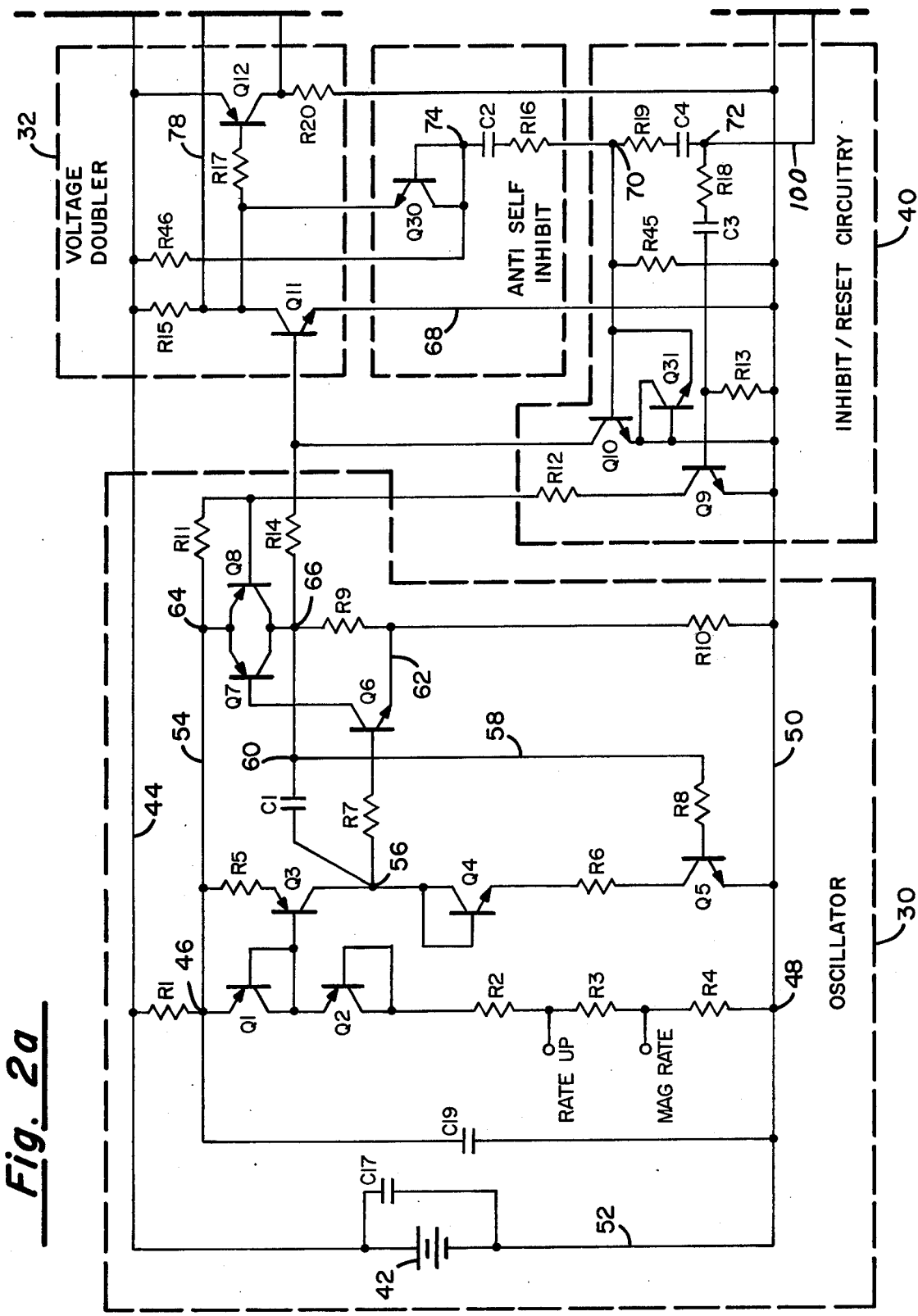
FIGS. 2a and 2b depict a preferred implementation of the system of FIG. 1.
Figure 2B:
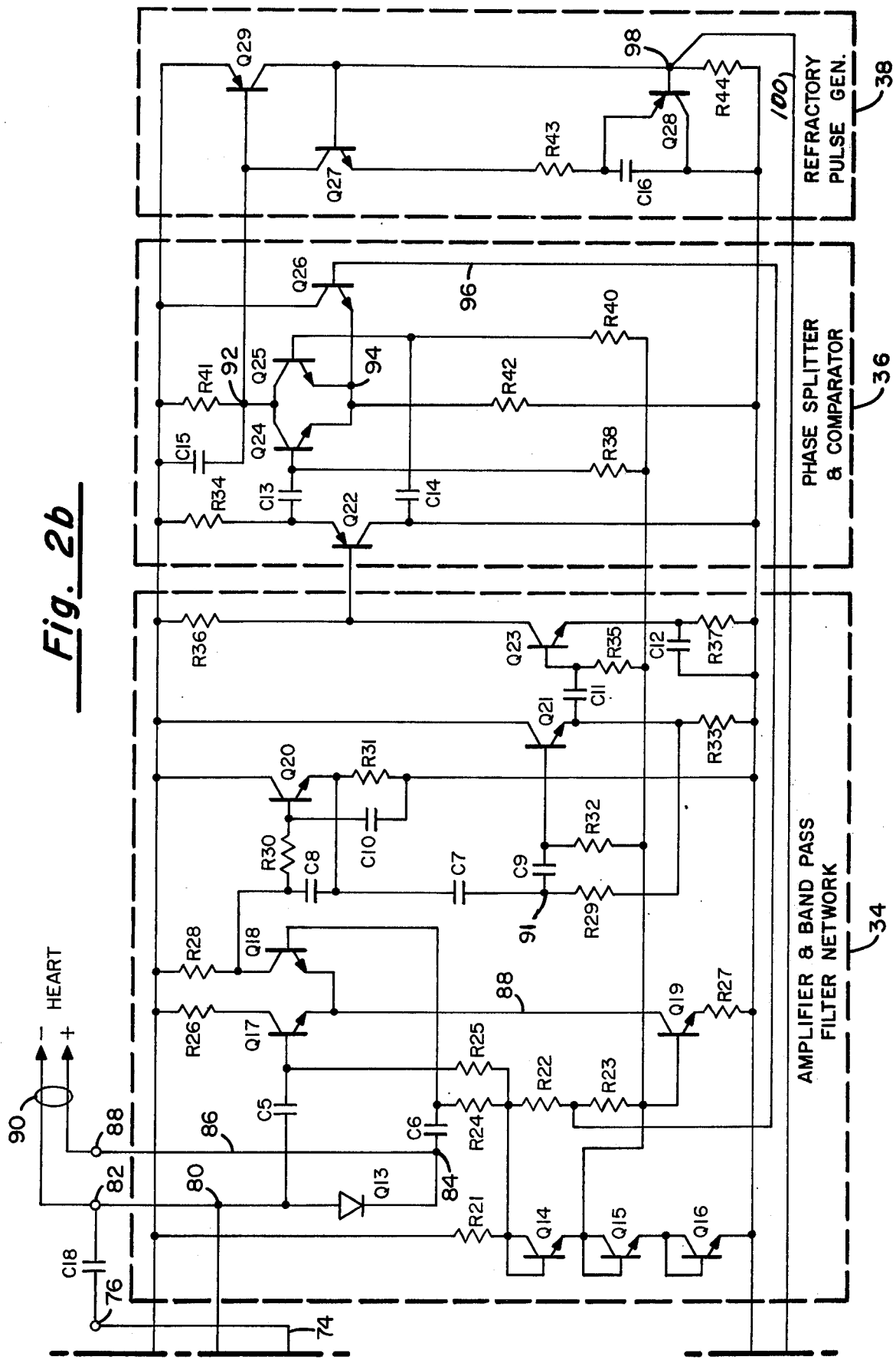

Referring now to FIGS. 2a and 2b there is illustrated a schematic diagram for implementing the block diagram of FIG. 1. Correlating the schematic of FIGS. 2a and 2b to the block diagram of FIG. 1, the circuitry corresponding to the astable multivibrator in FIG. 1 is shown as being enclosed by the broken line box 30 in FIG. 2a. Similarly, the voltage doubler pulser network is shown as being enclosed by the broken line box 32 in FIG. 2a. The amplifier, its associated biasing network and bandpass filter circuitry is shown as enclosed by the broken line box 34 in FIG. 2b. The level detector is shown as enclosed by the broken line box 36, and the refractory one-shot circuit in box 38 in FIG. 2b. The inhibit and reset circuitry is enclosed by the broken line box 40 in FIG. 2a.

Referring first to the multivibrator section enclosed by the broken line box 30, there is illustrated a battery type power source 42 which, in the preferred embodiment, may comprise a lithium-iodide solid state battery which, because of its long life and ability to deliver power without accompanying gas generation during discharge, is ideally suited for use as a power source of implantable pacers. Other power sources are, of course, suitable. Connected in parallel with the source 42 is a capacitor C17. Also connected in parallel with the energy source 42 is a constant current network which includes the series combination of resistors R1, R2, R3 and R4 along with transistors Q1, Q2, and Q3. The positive terminal of the battery 42 is connected to a terminal B+ which connects to the conductor 44 which serves as the B+ bus. The resistor R1 has one side connected to the bus 44 and the other side connected to the emitter electrode of transistor Q1 at a junction 46. The collector electrode of transistor Q1 is, in turn, connected to the emitter electrode of transistor Q2 as is the base electrode thereof. The base and collector electrodes of transistor Q2 are connected through the series combination of resistors R2, R3 and R4 to a junction 48 on the B— bus 50. The B— bus 50 is connected by a conductor 52 to the negative terminal of the energy source 42.

With the base electrodes of the transistors Q1 and Q2 connected respectively to their collector terminals, the transistors function as diodes and provide a predetermined voltage drop thereacross. Completing the constant current network is the transistor Q3. This transistor has its base electrode connected to the common junction between the base electrode and collector electrode of transistor Q1 and the emitter electrode of transistor Q2. The emitter electrode of transistor Q3 is coupled through a resistor R5 to a conductor 54 connected to the junction point 46. The collector electrode of transistor Q3 is connected to a junction 56 to which is also connected the base and collector electrodes of a transistor Q4. The emitter electrode of transistor Q4 is connected by means of a resistor R6 to the collector electrode of a transistor Q5 whose emitter is connected to the B— bus 50. Again, by connecting the base of transistor Q4 to its collector, the base-emitter diode of this transistor is effectively placed in series with the resistor R6.

The base electrode of transistor Q5 is coupled through a resistor R8 and a conductor 58 to a junction point 60. Connected between junction 56 and junction 60 is a timing capacitor C1.

The junction point 56 is coupled through a resistor R7 to the base electrode of a transistor Q6 whose emitter electrode is coupled by way of a conductor 62 and a resistor R10 to the B— bus 50. The collector electrode of transistor Q6 is connected to the base electrode of transistor Q7. The emitter electrode of Q7 is connected at a junction 64 to the emitter electrode of a transistor Q8 and to the conductor 54. The collector electrodes of transistors Q7 and Q8 are connected together and to a junction 66 which, in turn, is connected to the junction 60. A resistor R9 connects the junction 66 to the common point between conductor 62 and the resistor R10.

A resistor R11 is connected between the conductor 54 and the base electrode of transistor Q8 and a resistor R12 is connected in series with the emitter-to-collector path of a transistor Q9 to the base electrode of Q8. As will be described more fully hereinbelow, transistor Q9 forms part of the inhibit/reset circuitry.

The output from the astable multivibrator oscillator 30 appears at the junction point 66 and is coupled by means of the resistor R14 to the base electrode of transistor Q11 which forms part of the voltage doubler pulser network 32. The collector electrode of transistor Q11 is coupled through a resistor R15 to the B+ bus 44. The emitter electrode of transistor Q11 is tied to the B— bus 50 via conductor 68.

Also included in the inhibit/reset circuitry 40 is a transistor Q10 which has its collector electrode connected to the base electrode of transistor Q11 and its emitter electrode connected to the B— bus 50. Connected between the emitter electrode and the base electrode of transistor Q10 is the base-emitter diode of a transistor Q31. The base electrode of Q10 is also coupled by way of resistor R45 to the B— bus and to a junction point 70. A series combination of a resistor R19 and a capacitor C4 is connected between the junction 70 and a junction 72. Coupled between the base electrode of transistor Q9 and the junction 72 is a series combination of a capacitor C3 and a resistor R18. The base electrode of transistor Q9 is also coupled by way of resistor R13 to the B— bus 50.

The collector electrode of transistor Q11 is coupled by way of resistor R17 to the base electrode of a transistor Q12 in the voltage doubler pulser network 32. The emitter of transistor Q12 is tied to the B+ bus 44 and through a resistor R20 to the negative bus 50.

Connected between the junction 70 and the junction between the resistor R17 and the collector of transistor Q11 is a so-called "anti-self inhibit" circuit which includes a series connection of a resistor R16, a capacitor C2 and the base emitter diode of transistor Q30. The junction 74 between the capacitor C2 and the base/collector terminal of transistor Q30 and the positive bus 44 is a resistor R46.

The output from the voltage doubler pulser network 32 is obtained at the collector electrode of the transistor Q12 and is applied by way of a conductor 74 to an output terminal 76. The signal appearing at the collector electrode of the transistor Q11 is connected by way of conductor 78 to a junction 80 which, in turn, is connected to an output terminal 82 labelled "heart —". Junction 80 is coupled through a diode Q13 to a junction 84 and junction 84 is connected by conductor 86 to an output terminal 88 labelled "heart +". A capacitor C18 is connected between the terminal 76 and the terminal 82, this capacitor normally being a part of the electrode assembly rather than a component within the pacer circuit assembly or board itself. The terminals 82 and 88 are adapted to be connected to the heart of a patient by means of electrodes 90 which are surgically implanted in the heart of a patient who may be suffering from intermittent heart block. These electrodes not only serve to apply pacer pulses from the voltage doubler pulser network to the heart, but also serve the dual role of detecting or picking up the electrical signal produced by depolarization of the ventricular muscle and conveying such signals back through the terminals 82 and 88 to the junctions 80 and 84 which comprise the input terminals of the amplifier and bandpass filter network 34.

The biasing network for the amplifier 34 is provided by the series combination of a resistor R21 and the transistors Q14, Q15 and Q16 each of which has its base electrode connected to its collector electrode to function as a diode. This series circuit is connected between the positive bus 44 and the negative bus 50.

Junction 80 is coupled by means of a capacitor C5 to the base electrode of a transistor Q17 which is also coupled to the bias network previously described by means of a resistor R25. In a similar fashion, the junction 84 is coupled through a capacitor C6 to the base electrode of a transistor Q18 which is coupled to the bias network by way of resistor R24. The emitter electrodes of transistors Q17 and Q18 are tied together and their respective collector electrodes are individually coupled through resistors R26 and R28 to the B+ bus 44. As such, transistors Q17 and Q18 act as a difference amplifier of the signals picked up from the heart. The common junction between the emitter electrode of transistors Q17 and Q18 is connected by conductor 88 to the collector electrode of a transistor Q19. The emitter electrode of transistor Q19 is coupled through resistor R27 to the B— bus 50. A voltage divider comprised of resistors R22 and R23 provides the bias for the transistor Q19.

The difference output signal appearing at the collector electrode of transistor Q18 is applied to the input of an active bandpass filter which includes a transistor Q20, a resistor R31 and capacitors C8 and C10. More specifically, the base electrode of the transistor Q20 is coupled through a resistor R30 to the collector electrode of the transistor Q18. Transistor Q20 is an emitter follower stage and the output which appears at the emitter terminal thereof is fed back via capacitor C8 to the input of the active filter network. Capacitor C10 couples the base electrode of the transistor Q20 to the negative bus 50. The output developed across the emitter follower resistor R31 is also coupled by way of capacitor C7 to a junction 91.

The junction 91 is capacitively coupled through capacitor C9 to the base electrode of the emitter follower amplifier stage consisting of transistor Q21 and resistor R33. The emitter follower transistor Q21 is normally biased by means of the current flowing through resistor R32 which is coupled to the aforementioned bias network. For stable operation, a portion of the output signal which is developed at the emitter electrode of transistor Q21 is fed back by way of resistor R29 to the junction 91.

The output from the emitter follower stage Q21 is capacitively coupled via capacitor C11 to the base electrode of a Class A amplifier stage which includes the transistors Q23 and Q22. More specifically, a resistor R36 couples the collector electrode of the transistor Q23 to the B+ bus 44 and a resistor R37 connects the emitter electrode of transistor Q23 to the negative bus 50. A capacitor C12 is connected directly in parallel with the resistor R37. The base of the transistor Q23 is biased for Class A operation by way of the current flowing from the bias network through resistor R35. The collector of transistor Q23 is directly connected to the base electrode of the transistor Q22 contained within the broken line box 36. Transistor Q22 along with the resistors R34 and R39 comprise a phase splitting network. More specifically, the emitter electrode of transistor Q22 is connected to the bus 44 by way of resistor R34 and its collector electrode is connected to the negative bus 50 by way of resistor R39.

The level detector, also shown as being enclosed by dashed line box 36, includes the transistors Q24 and Q25 and their associated input and bias connections and the transistor Q26 which, in effect, acts as a comparator. More specifically, the signal appearing at the emitter electrode of transistor Q22 is coupled by way of capacitor C13 to the base electrode of transistor Q24. The signal appearing at the collector electrode of transistor Q22 is coupled through capacitor C14 to the base electrode of transistor Q25. The collector electrodes of transistors Q24 and Q25 are connected together at a junction 92 which, in turn, is connected to the B+ bus 44 through the parallel combination of resistor R41 and capacitor C15. Bias to the stage Q24 is provided via resistor R38 and, similarly, bias for transistor Q25 is provided through resistor R40 which connects the base of transistor Q25 to the bias network previously described. The emitter electrodes of transistors Q24 and Q25 are connected together at a junction 94 and through a resistor R42 to the negative bus 50.

Junction 94 is connected to the emitter electrode of transistor Q26 and the collector thereof is tied directly to the B+ bus 44. The base of transistor Q26 is connected through conductor 96 back to the midpoint of the voltage divider consisting of resistors R22 and R23.

The refractory pulse generator shown enclosed by broken line box 38 includes the regeneratively coupled transistor pair Q27 and Q29, resistors R43 and R44, capacitor C16 and the semiconductor switch Q28. The input to this network is obtained at the junction 92 and is coupled to the base electrode of Q29 whose emitter electrode is tied directly to the positive bus 44. The collector electrode of transistor Q29 is connected to the base electrode of transistor Q27 and to a junction 98 between the base electrode of transistor Q28 and one terminal of the resistor R44. The other terminal of resistor R44 is connected directly to the negative bus 50. The collector electrode of the transistor Q27 is connected to the base electrode of Q29 and its emitter is coupled through the series combination of resistor R43 and capacitor C16 to the negative bus 50. The capacitor C16 is connected directly between the emitter and collector electrodes of the semiconductor switch Q28. The outputs from the refractory one-shot circuit is obtained at the junction 98 and is coupled by way of conductor 100 back to the junction 72 in the inhibit/reset circuit 40.

Now that the details of the construction of the cardiac pacer circuit have been described, consideration will next be given to its mode of operation.

OPERATION — FIGS. 2a AND 2b

As was described in connection with the block diagram of FIG. 1, the circuit of the present invention is operative to provide artificial stimulating pulses to the heart muscle, only in the absence of normal heart activity in the patient. When the heart of the patient is operating normally, the pacer network is precluded (inhibited) from applying artificial pulses thereto. In understanding the mode of operation of the circuitry of FIGS. 2a and 2b, let it first be assumed that the patient's heart is not operating normally to produce depolarization signals of a sufficient amplitude or with sufficient regularity, and that artificial stimulation is therefore needed.

The battery source, when connected between the terminals B+ and B− causes a current to flow through the resistor R1, the emitter-base junctions of transistors Q1 and Q2 and the resistors R2, R3 and R4 causing a relatively constant current to be developed at the junction 56 independent of changes in the impedance which may be presented to this junction during operation of the oscillator network 44. If operation is considered to begin at the time that capacitor C1 is fully discharged and transistors Q5, Q6 and Q7 are all nonconducting, capacitor C1 will begin to charge up by a current flowing from the junction 56, through C1 and resistors R9 and R10. As capacitor C1 charges up, a point is reached where transistor Q6 will become forward biased by the current flowing through resistor R7, the base-to-emitter path of transistor Q6 and resistor R10. Transistor Q6 will then begin to conduct, sinking the base current of transistor Q7 through resistor R10 to the negative bus 50. Transistor Q7 therefore turns on, connecting the base of transistor Q5 to the relatively positive conductor 54. This action causes base current to flow into transistor Q5, turning it on. Once Transistor Q5 is conducting, capacitor C1 will discharge rapidly, and thereafter begin to rapidly charge in the opposite polarity through the transistor Q4, the resistor R6, and the transistor Q5. After a time determined by the relative magnitude of these resistances and the value of capacitor C1, the potential on the base of transistor Q6 falls below the conducting maintenance threshold of transistor Q6 and it turns off. With Q6 nonconducting, Q7 will be turned off as will be transistor Q5, thereby completing the cycle.

When transistor Q11 is nonconducting, current flows from the B+ bus 44 through resistor R15, the "heart −" terminal 82, the capacitor C18, the terminal 76, the conductor 74 and the resistor R20 to charge capacitor C18 with the polarity indicated. When transistor Q11 is turned on by the positive pulse produced at the junction 66 when transistor Q7 is turned on, transistor Q12 will also be turned on, thereby completing the following path:

From the B+ bus 44, the emitter-to-collector path of transistor Q12, conductor 74, capacitor C18, junction 82, junction 80, conductor 78, and the collector-to-emitter path of transistor Q11, through the B− bus 50 back to the negative terminal of the source 42.

Thus it can be seen that the potential on the battery is added to that which is stored in the capacitor C18 and applied across the heart electrodes 90. Hence, the pulse applied to the heart will be approximately twice the potential of the source 42.

Next, let it be assumed that the patient's heart is beating normally to produce depolarization signals across the heart electrodes 90.

Current from the B+ bus 44, through resistor R21 and the diode connected transistors Q14, Q15 and Q16 to the B-bus 50 constitutes a voltage divider type bias network. Equal value resistors R24 and R25 normally maintain the base electrodes of transistors Q17 and Q18 at the same potential in the quiescent state. Transistor Q19 is biased on.

Depolarization of the heart muscle can result in either positive or negative going signals hereinafter referred to as "bipolar" signals. The difference amplifier comprised of transistors Q17 and Q18 is responsive only to the potential difference existing between the junctions 80 and 84 so that it is immaterial which terminal is positive with respect to the other. At the time that the heartbeat occurs, a potential difference existing between junctions 80 and 84 will be coupled via capacitors C5 and C6 to the base electrodes of the transistors Q17 and Q18. The output appearing at the collector electrode of transistor Q18 will therefore be proportional to the difference between the signal applied to the base of transistor Q17 and that applied to the base of transistor Q18. The difference amplifier is designed to provide a high degree of rejection to so-called "common-mode" noise signals. The resulting difference signal is applied to the input of the active bandpass filter which includes resistor R30, transistor Q20, and capacitors C8 and C10. Only a signal having a prescribed frequency characteristic will pass through this amplifier and signals having other frequency characteristics will be attenuated. The output from the active bandpass filter network is coupled through capacitor C7 to the junction point 91. This signal is capacitively coupled through capacitor C9 to the base of the emitter follower stage Q21.

The output of stage Q21 is, in turn, capacitively coupled via capacitor C11 to the input of a Class A amplifier stage Q23. Transistor Q23 is biased to operate in a linear range. If the output from transistor Q21 is a positive going signal, conduction through transistor Q23 increases, causing conduction through the phase-splitter transistor Q22 to also increase. This causes a positive going signal to be applied by way of capacitor C14 to the base of transistor Q25, turning it on and causing a negative pulse to appear at the junction point 92. If the signal from transistor Q21 was such as to cause the conduction in transistor Q23 to decrease, conduction through transistor Q22 would also decrease causing a positive signal to appear at its emitter. This positive signal would be coupled through capacitor C13 to the base of transistor Q24, turning on transistor Q24 and also producing a negative pulse at the common collector junction 92. Thus, no matter what the polarity of the bipolar depolarization pulse applied to the difference amplifier (transistors Q17 and Q18), a negative going pulse will always appear at the junction 92.

The input level at which the transistors Q24 and Q25 will turn on is controlled by the comparator transistor Q26. This transistor is normally biased to hold the emitters of transistors Q24 and Q25 at a preset positive potential. Only if the positive signals at either of the base electrodes of transistors Q24 or Q25 exceed the established threshold will either transistor Q24 or Q25 conduct. The particular level is established by trimming the resistor R23 to a level to yield the desired mode of operation.

Assuming that the depolarization pulse is sufficiently large to overcome the preset bias established by the comparator transistor Q26, a negative going pulse will be applied to the base electrode of transistor Q29, thereby driving it into conduction. This raises the potential on the base of transistor Q27 turning it on and, in a regenerative fashion, snapping transistor Q29 into saturation. With transistors Q29 and Q27 fully conducting transistor Q28 will be turned off, removing the short circuit across the capacitor C16. Capacitor C16 will then begin to charge from the current flowing from the B+ bus 44 through resistor R41, the collector-to-emitter path of transistor Q27 and R43 to the negative bus 50. As capacitor C16 becomes charged, a point is reached where transistor Q27 turns off. This, in turn, opens the base current circuit for transistor Q29 and transistor Q29 will also turn off. With transistor Q29 nonconducting, transistor Q28 again resumes conduction, causing capacitor C16 to be rapidly discharged. Thus, the refractory pulse generator is operative upon being triggered by a negative input to produce a positive going pulse of a predetermined duration determined by the RC time constant of capacitor C16 and resistors R41 and R43. The duration of this pulse can be controlled to a high degree of accuracy by trimming the value of resistor R43 during final testing of the assembly and prior to implantation.

The leading edge of the refractory pulse which appears at the junction 98 when transistor Q29 is snapped on is coupled by way of conductor 100, resistor R18 and capacitor C3 to the base electrode of transistor Q9. This positive going signal turns on transistor Q9 which, in turn, causes transistor Q8 to also turn on. When transistor Q8 turns on, transistor Q5 will also be rendered conductive no matter what the condition of the charge on capacitor C1 might be at the time. With transistor Q5 conducting, capacitor C1 discharges through R6 and Q5 to ground, thereby resetting the multivibrator.

The leading edge of the refractory pulse is also coupled through capacitor C4 and resistor R19 to the base of transistor Q10 turning it on and clamping the base of transistor Q11 to ground. Transistors Q11 and Q12 are thereby held off during the reset operation which inhibits the generation of a pacer pulse across the terminals 82 and 88. The voltage divider resistors R19 – R45 and R18 – R13 are chosen to ensure that Q10 will be turned on ahead of Q9. Thus, the inhibit function takes place prior to the reset function.

The anti-self inhibit circuitry which includes the diode connected transistor Q30, capacitor C2 and the resistor R16 is included to ensure that a full width pacer pulse will be produced in the absence of a normal heartbeat. In the absence of the anti-self inhibit circuit, it is possible for a pulse from the multivibrator to pass through the difference amplifier stages Q17 and Q18 to ultimately trigger the refractory pulse generator in the manner described. This creates a race condition and the leading edge of the refractory pulse could reset the multivibrator and inhibit the pulser output before a full pacer pulse has been produced across the heart terminals 82 and 88. In operation, when Q11 turns on, its collector goes negative and this negative signal is coupled through the diode Q30, capacitor C22 and resistor R16 to hold the base of transistor Q10 sufficiently negative to prevent Q10 from turning on even when the positive leading edge of the refractory pulse is applied via capacitor C4 and resistor R19 to the base of transistor Q10. As long as Q10 is nonconducting, the transistors Q11 and Q12 will remain on to deliver a full width pacer pulse to the heart.

Figure 3:
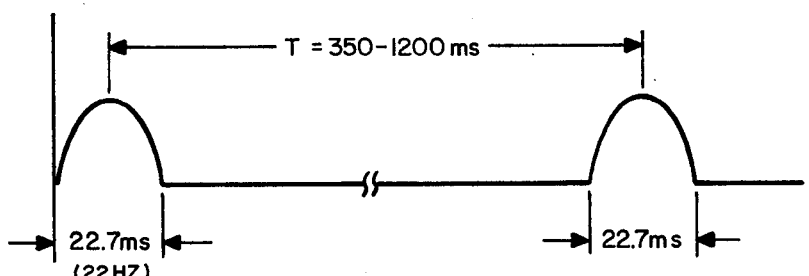
FIG. 3 is a waveform illustrating the characteristics of a typical R-wave output signal normally received by the heart.
Figure 4:
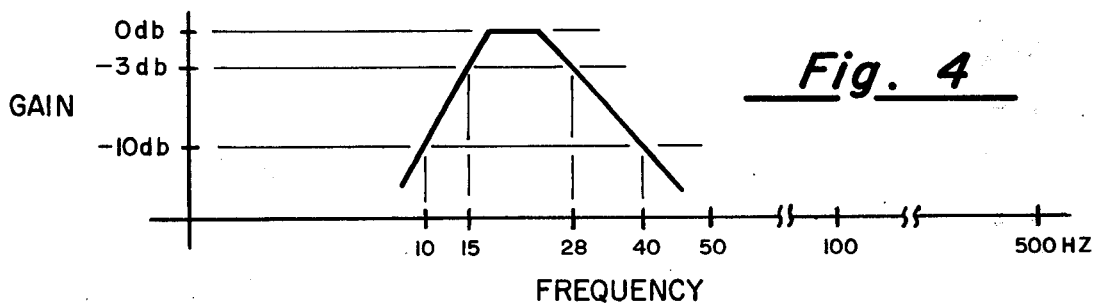
FIG. 4 illustrates the frequency response of the operational amplifier used in the system.

Referring now to FIG. 3, there is shown a typical R-wave simulation signal produced by a normally functioning heart. It can be seen from this figure that the pulse width of this signal corresponds to a center frequency of approximately 22 Hz. Successive bats produced by successive R-wave depolarization signals are separated from one another by a time period, T, equal to a value in the range of from 350 to 1200 milliseconds, depending upon the physical activity of the patient. Referring next to FIG. 4, there is shown a curve depicting the output from the bandpass amplifier network 34 as a function of frequency. By properly choosing the values of the capacitors C8, C10, C7 an C9 and the resistors R31 and R30, a rather sharp passband for the amplifier network 34 can be obtained. Capacitors C8 and C10 control the high frequency roll-off characteristics while capacitors C7 and C9 are chosen to yield a desired low frequency roll-off. As is indicated in FIG. 4, when the frequency differs from the center frequency of 22 Hz by only about 7 Hz, the gain has already dropped off by 3 db. It should also be noted that the gain has dropped to a significantly low level well before the point where high noise concentration is commonly found in the frequency spectrum. Thus, the selectivity of the bandpass amplifier network 34 insures that only R-wave signals produced by the heart will be amplified and that most commonly encountered noise signals induced on the implanted electrodes 90 will be attenuated below a level needed to trigger the one-shot circuit.

Figure 5:
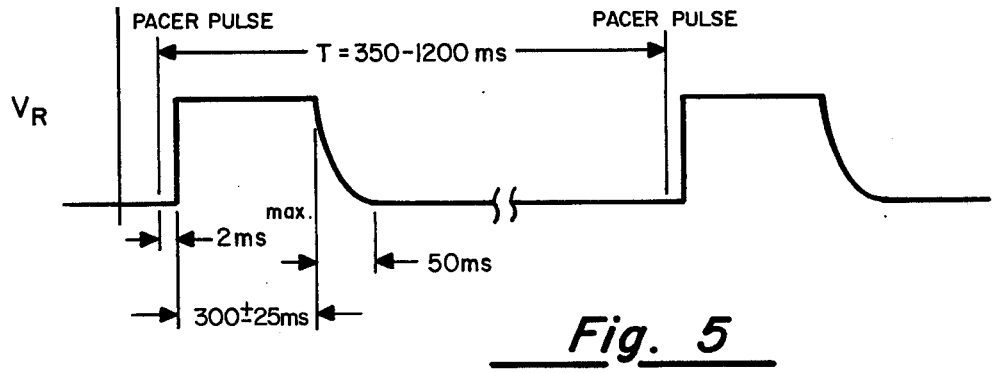
FIG. 5 illustrates the waveform of the output obtained from the refractory one-shot circuit.

Referring now to FIG. 5, there is shown the waveform of the signal appearing at junction 98, the output from the refractory pulse generator 38. In the preferred embodiment of the invention with the components chosen, approximately 1 millisecond elapses from the time that the refractory pulse is generated until the reset and inhibit functions have been accomplished. Reference to FIG. 5, however, reveals that the refractory pulse is designed to persist for an extended period beyond this 1 millisecond. The purpose for the additional width of the refractory pulse is to preclude reinitiation of additional refractory cycles. This is a significant feature where spurious pulses may be generated by the system through a combination of pulser noise and/or ringing in the amplifier network 34. Unless there is sufficient width to the refractory pulse to allow time for this noise to decay, the system could possibly regenerate its own refractory pulse independent of the occurrence of a natural R-wave depolarization signal.

Should the rare occurrence happen that the ambient electrical noise picked up on the electrodes 90 is in the passband of the active bandpass filter network, it is desirable that the pacer network switch over from a demand-inhibit mode to an asynchronous mode such that artificial stimulating pulses will be produced irrespective of normal heart activity. In the present invention, this type of operation is provided by the judicious selection of the values of capacitors C3 and C4. More specifically, by using relatively large values for capacitors C3 and C4, a recovery period is introduced between the trailing edge of one refractory period and the time when the leading edge of the next succeeding refractory pulse can reinitiate the resetinhibit operation. Therefore, it the noise pulses are occurring at a frequency in the range from 20 to 30 Hz and are thereby getting through the filter, the base electrodes of transistors Q9 and Q10 will remain negative, holding them off even during the transition of the noise signals between the positive and negative threshold levels established by transistor Q26 or transistors Q25 and Q24. So long as transistors Q9 and Q10 are conconductive, the voltage doubler pulser 32 will function to produce pacer pulses at a rate determined by the oscillator 30, with R41 and C15 integrating noise and keeping Q29 conductive, thus holding the refractory line high.

In a practical embodiment of this invention, the components of the described apparatus may have the following values:

| | |
|---|---|
| R1 | 51 K |
| R2, 3, 4, 26 | 500 K |
| R5 | 7.5 K |
| R6 | 2,5 K |
| R7, 8, 10 | 20 K |
| R9 | 40 K |
| R11, 12, 13, 27 | 30 K |
| R14, 15, 17, 20 | 5 K |
| R16, 18, 19 | 50 K |
| R21, 22, 28, 30, 31, 32, 33, 39, 41, 44 | 1 M |
| R23 | 100 M |
| R24, 25, 35, 37, 38, 40 | 2 M |
| R29 | 140 K |
| R34 | 800 K |
| R36 | 3 M |
| R42 | 200 K |
| R43 | 300 K |
| R2, 3 and 4 trimmed to yield a pulse rate of 72 beats/min. | BOL |
| C1, 16 | 0.27 uf |
| C2, 5, 6, 11, 13, 14 | 0.027 uf |
| C3 | 0.01 uf |
| C4, 7, 9 | 0.02 uf |
| C8 | 0.022 uf |
| C10 | 0.00330uf |
| C12 | 0.033 uf |
| C15 | 0.002 uf |
| C17 | 100 uf |
| C18, 19 | 18 uf |
| Q1, 2, 3, 7, 8, 22, 28, 29 | 2N5087 |
| Q4, 5, 6, 9, 10, 14, 15, 16, 19, 20, 21, 23, 26, 27, 30, 31 | 2N2484 |
| Q11 | 2N2222 |
| Q12 | 2N2901 |
| Q17, 18, 24, 25 | 2N4044 |

DESCRIPTION OF THE ALTERNATE PREFERRED EMBODIMENT

Figure 6A:
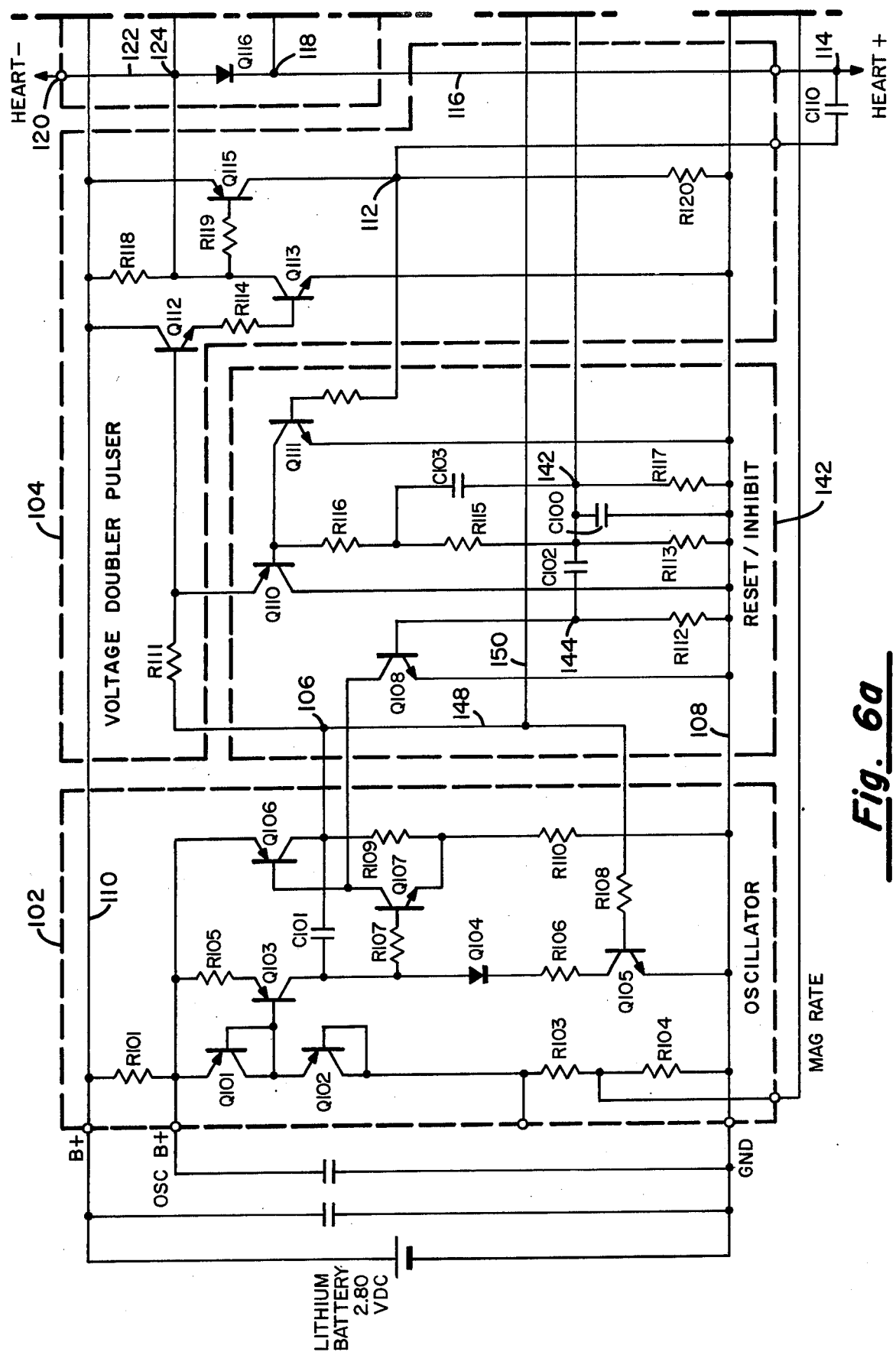
FIGS. 6a and 6b depict an alternate preferred embodiment of the system of FIG. 1.
Figure 6B:
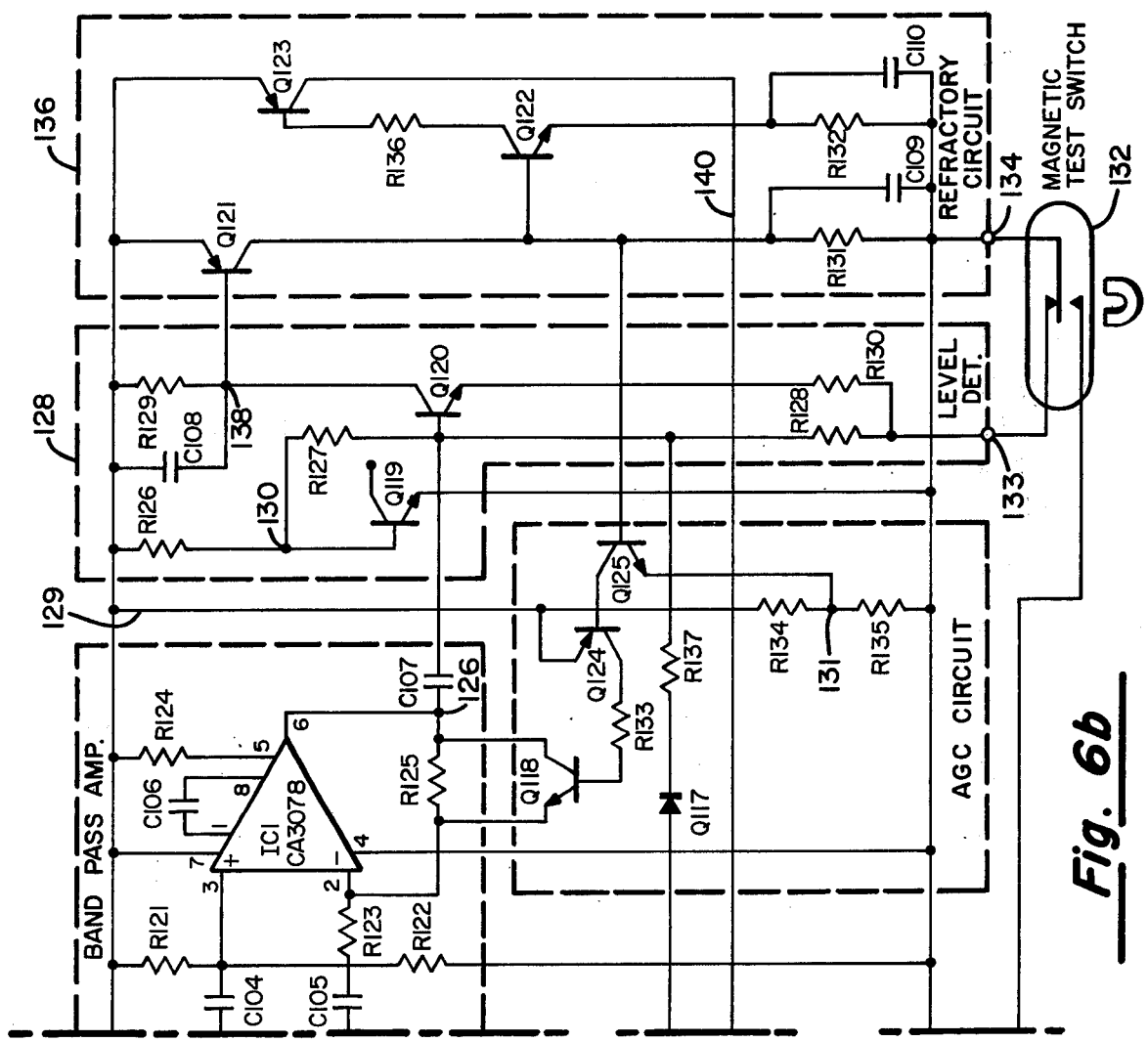

Referring now to FIGS. 6a and 6b, there is shown an alternate arrangement of the cardiac pacer in accordance with the teachings of the present invention.

Again, for convenience, the circuit has been partitioned by broken line boxes into functional components. More specifically, there is shown enclosed by broken line box 102 the oscillator portion of the pacer circuit. Oscillator 102 is substantially identical to the oscillator network 30 of FIG. 2 in its construction and mode of operation so that it should not be necessary to repeat the description thereof.

The voltage doubler pulser network is shown enclosed by broken line box 104 and includes the semiconductor switching transistors Q112, Q113, and Q115. The output from the oscillator network appearing at the junction 106 is coupled by way of a resistor R111 to the base electrode of the NPN transistor Q112. The collector of this transistor is connected to the B+ bus 110 and the emitter electrode thereof is coupled through a resistor R114 to the base electrode of transistor Q113. The collector electrode of transistor Q113 is coupled to the B+ bus 110 via resistor R118 and the emitter electrode of transistor Q113 is tied to the ground bus 108. A resistor R119 couples the collector electrode of transistor Q113 to the base electrode of a PNP transistor Q115 which has its emitter electrode also tied to the B+ bus 110 and its collector electrode tied to a junction point 112. Junction point 112 is coupled through a resistor R120 to the group bus 108 and to a first terminal of the voltage doubler capacitor C110. The other terminal of capacitor C110 is tied to the "Heart +" terminal 114 which is adapted to be connected to the implanted electrodes which are used to couple the pacer circuit to the heart of the patient. Terminal 114 is also connected by a conductor 116 to a junction point 118. The "heart -" terminal 120 which is also connected by the implanted electrodes to the heart of the patient is connected by a conductor 122 to a junction point 124. Connected between junction 118 and 124 is a semiconductor diode Q116 which is poled as shown in the drawings. A capacitor C105 and a resistor R123 connect the junction point 118 to the complementary input terminal of the operational amplifier IC1. A capacitor C104 couples the junction point 124 to the positive input terminal of the integrated circuit differential operational amplifier IC1 and a resistor R121 is used to complete the B+ bus 110 to the positive input terminal of the amplifier. Amplifier IC1 is a commercially available unit and may be a Type CA-3078H amplifier chip manufactured and sold by RCA of Sommerville, N.J. Since such an amplifier is commercially available, it is not believed to be necessary to describe in detail the circuitry embodied in it, and it should suffice to say that it function as a differential bandpass amplifier having relatively sharp cut-off characteristics when connected as shown. The capacitor C106 is chosen to provide a desired gain roll-off characteristic at the high end of the frequency band whereas the capacitors C104 and C105 provide the corresponding roll-off in the output at the low end of the passband.

An NPN transistor Q118 having its emitter-to-collector path connected in parallel with the resistor R125 forms part of an automatic gain control circuit for the operational amplifier IC1. Also included in this AGC loop are transistors Q124 and Q125. The collector of PNP transistor Q124 is coupled through a resistor R133 to the base or control electrode of transistor Q118 and the emitter electrode of transistor Q124 is directly connected to the B+ bus 110 by a conductor 129. The emitter of Q124 is coupled to the B- bus 108 via a voltage divider including resistors R134 and R135. The base electrode of transistor Q124 is connected to the collector of electrode of NPN transistor Q125 and the emitter is tied to the output junction 131 of the aforementioned voltage divider.

The output signal appearing at junction 126 is coupled by way of a capacitor C107 to the base electrode of the level detector transistor Q120 contained within the level detector network enclosed by broken line box 128. Also included in the level detector network 128 is a voltage divider which includes a resistor R126 connected in series with a diode connected transistor Q119 between the B+ bus 110 and the ground bus 108. A resistor R127 is connected between the common terminal 130 between the resistor R126 and the diode connected transistor Q119 and the base electrode of the level detector transistor Q120. A resistor R128 is connected between the base electrode of the transistor Q120 and a first terminal 133 which is adapted to be connected to a first pole of a normally closed magnetic-type reed switch 132, the other pole of which is adapted to be connected to a terminal 134 which is connected to the ground bus 108. Thus, when the switch 132 is closed as illustrated, the resistor R128 connects the base electrode of the level setting transistor Q120 to ground. A parallel combination of a capacitor C108 and a resistor R129 couple the collector electrode of transistor Q120 to the B+ bus 110. A resistor R130 couples the emitter electrode of transistor Q120 to the terminal 130.

The refractory circuit is shown enclosed by dashed line box 136 and includes the transistors Q121, Q123 and Q122. Also included in the refractory circuit are timing networks which include the capacitor C109, the resistor R131, the capacitor C110 and the resistor R132. More specifically, the output from the level detector network appears at a junction point 138 to which is connected the base electrode of a PNP transistor Q121. The emitter electrode of transistor Q121 is tied to the B+ bus 110 and its collector electrode is connected through the parallel combination of resistor R131 and capacitor C109 to the negative bus 108. The collector electrode of transistor Q121 is also connected to the base electrode of NPN transistors Q122 and Q125. The emitter electrode of transistor Q122 is coupled through the timing circuit comprised of capacitor C110 and resistor R132 to the ground bus 108. Its collector electrode is connected via resistor R136 to the base electrode of transistor Q123. The emitter electrode of transistor Q123 is connected to the B+ bus 110 and its collector electrode is coupled by a conductor 140 back to the reset/inhibit network shown enclosed by broken line box 142.

The reset/inhibit network 142 includes the semiconductor switching transistor stages Q108, Q110 and Q111. More specifically, the conductor 140 connects the collector electrode of the refractory transistor Q123 to a junction point 142 which is, in turn, coupled to the ground bus 108 by means of a parallel combination of capacitor C100 and resistor R117. Junction 142 is also coupled by way of a capacitor C102 to a junction point 144 formed between the series connected resistor R112 and the base electrode of the transistor Q108. The resistor R112 has its other terminal connected to the ground bus 108. The emitter electrode of transistor Q108 is tied to the ground bus 108 and the collector electrode thereof is connected directly to the common point between the collector electrode of transistor Q107 and the base electrode of transistor Q106, both of which are in the oscillator portion of the circuit 102.

The junction point 142 is also coupled via capacitor C103 to a tap 146 which is a point on the voltage divider comprises of series resistors R113, R115 and R116. A resistor is connected directly to the base electrode of transistor stage Q111 and to the junction 112. Transistor Q111 has its emitter electrode tied to the ground bus and its collector is tied to the base electrode of transistor stage Q110. The emitter electrode of transistor Q110 is connected directly to the base electrode of transistor Q112 in the voltage doubler pulser network 104 and the collector electrode of transistor Q110 is tied directly to the ground bus 108.

Finally, a semiconductor diode Q117 and a resistor R137 are connected by conductors 148 and 150 between the junction point 106 and the base electrode of the level detector transistor stage Q120.

Now that the details of the construction of the alternate preferred embodiment of the invention has been described in detail, consideration will next be given to its mode of operation.

OPERATION — FIG. 6a and 6b

In explaining the operation of the circuit of FIGS. 6a and 6b, let it first be assumed that the heart is not functioning normally to produce depolarization signals across the terminals 114 and 120 such that artificial stimulation is required. The combination of the lithium-iodide energy source, the resistors R101, R103, R104, and R105, and the transistors Q101, Q102 and Q103 comprise a constant current source which supplies a constant charging current to the timing capacitor C101, independent of variations in load or supply voltage. Other battery sources may be employed in this circuit usefully. Capacitor C101 begins to charge up by the current which flows through it and through the resistors R109 and R110. After a predetermined interval determined by the time constant of this path, a point is reached where transistor Q107 will be turned on. Once this stage turns on, a path is provided for the base current of transistor Q106 and this stage quickly is driven into its saturated state. Once transistor Q106 is conducting, a positive signal will be applied to the junction 106 and from there to the base of the transistor stage Q105 by way of coupling resistor R108. Transistor Q105 therefore turns on and provides a low resistance discharge path for the timing capacitor C101. As capacitor C101 discharges through diode Q104, resistor R106 and the now-conducting transistor Q105, a point will be reached at which the potential on the base electrode of transistor Q107 will no longer be sufficient to sustain conduction therethrough and it will turn off. When transistor Q107 turns off, Q106 and Q105 also turn off to complete the cycle. Hence, the oscillator functions to produce a short duration pulse at predetermined intervals determined primarily by the magnitude of the capacitor C101 and the resistor R110.

The short positive pulse emanating from the oscillator network 102 appears at junction 106 and is applied to the base electrode of the voltage doubler pulser transistor Q112 via resistor R111. During the interval that transistor Q112 is off, the capacitor C110 becomes charged to approximately the potential of the battery source. This charging path includes the resistor R118, diode Q116 and resistor R120. The positive pulse from the oscillator 102 turns the transistor Q112 on such that base current is provided to the switching transistor Q113 and it also turns on. Once transistor Q113 is conducting, its collector electrode goes to ground, allowing transistor Q115 to also turn on. As a result, a voltage equal approximately to the sum of the battery voltage and the voltage on the capacitor C110 is applied across the "heart +" terminal 114 and the "heart —" terminal 120. That is, when both transistors Q113 and Q115 are conducting, a path is established from the B+ bus 110 through transistor Q115, through the capacitor C110 and from the "heart +" terminal 114 through the heart load to the "heart —" terminal 120 and from there through conductor 122 and the conducting transistor Q113 back to the ground bus 108. Thus, the combination of the oscillator network and the voltage doubler pulser network operate in the absence of normal heart activity to apply a stimulating pulse equal in amplitude to approximately twice the battery voltage to the implanted heart electrodes.

Now, let it be assumed that normal heart activity is present so that an understanding can be had of the mode of operation of the inhibiting circuitry used to prevent artificial stimulation when the heart is beating normally.

As in the embodiment of FIGS. 6a and 6b, the bipolar signals developed during the ventricular depolarization of the heart muscle are picked up by the implanted electrodes and applied to the terminals 114 and 120. These signals are coupled to the bandpass differential amplifier IC1 by means of the capacitors C104 and C105 and the resistor R123. Since the component values of these last-mentioned components as well as the value of capacitor C106 are set to define a passband which will permit amplification of the normal heart depolarization signals, an output will appear at the terminal 126 which is proportional to the difference between the voltage signals applied to the positive and negative input terminals of amplifier IC1. The values of resistors R126, R127, R128 and the diode connected transistor Q119 are set to cause the base of the level detector transistor Q120 to be biased at approximately 0.15 volt. A positive pulse emitted from the differential amplifier IC1 will cause momentary conduction in transistor Q120. If the pulse is of sufficient amplitude, then transistors Q121, Q122, Q123 all turn on and the resulting positive signal which appears on conductor 140 is coupled back through capacitor C102 to turn on transistor Q108. With transistor Q108 conducting, a negative potential is applied to the base of transistor Q106 and it too begins to conduct. As was explained in connection with the operation of the oscillator section 102, as soon as transistor Q106 is conducting, transistor Q105 also is turned on to discharge the capacitor C101 no matter where in the cycle of operation of the oscillator the refractory pulse on conductor 140 appears.

The turning on of transistor Q106 causes junction 106 to assume a more positive potential such that the diode Q117 conducts. This action causes the base of transistor Q120 to assume a positive potential of approximately 2.4 volts. This regeneration action on transistor Q120 assures that transistor Q121 and transistor Q106 fully saturate so as to completely charge capacitors C109 and C108. This type of operation is essential to assure a predictable delay establishing a proper pulse width to the refractory signal appearing on conductor 140.

For this regeneration action to function ideally, it is desirable that the forward gain of the operational amplifier IC1 should be low, approaching or approximating zero. The AGC circuit including transistor switch Q118 connected as shown from the output terminal 126 back to the complementary input terminal of the amplifier serves to approximate this condition. More specifically, when no R-wave pulse is present at the output of the amplifier IC1, transistor Q121 is nonconducting and the base electrode of transistor Q125 is low, with respect to its emitter and, hence, it too is nonconducting. With transistor Q125 nonconducting, transistor Q124 will also be off, since there is no base current sink therefor. For the same reason, transistor Q118 will also be off and the feedback resistor R125 will be in the amplifier circuit and the gain of the amplifier will be high. However, when an R-wave or an artificial stimulating pulse is applied to the amplifier IC1 inputs, the threshold detector will cause transistor Q121 to conduct. This, in turn, turns on transistors Q125, Q124 and Q118 to short out the resistor R125, causing the gain of the amplifier to become relatively low.

Figure 7:
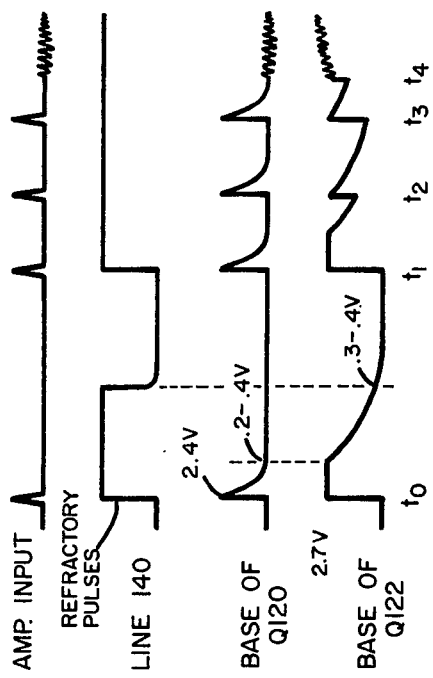
FIG. 7 is an exemplary waveform useful in explaining the operation of the circuit of FIGS. 6a and 6b.

Referring now to FIG. 7 which illustrates various waveforms observed in the circuit of FIGS. 6a and 6b a normal input pulse from the heart to the amplifier causes the refractory pulse to go positive, causing a resetting of the oscillator section 102 (as previously described) and the charging of capacitors C108 and C109. After approximately 1 millisecond has elapsed from the time that the refractory pulse is generated, transistor Q106 is turned off because of the discharge of capacitor C101. At this time, capacitor C107 begins to lose its charge through resistors R127 and R128 and after about 60 milliseconds, the turn-off threshold of transistor Q120 is reached. When transistor Q120 ceases to conduct, transistor Q121 is also turned off such that capacitor C109 is no longer receiving a charging current. The charge on capacitor C109 begins to leak off through resistor R131. After about 240 milliseconds established by the time constant product of capacitor C109 and resistor R131, the turn-off threshold of transistor Q122 is reached. When transistor Q122 ceases to conduct, transistor Q123 is simultaneously rendered non-conductive and the potential appearing on conductor 140 again goes low, terminating the refractory period.

Summarizing then, when the normal heart activity is such as to cause the operational amplifier to output a signal which exceeds a threshold established by the turn-on point of transistor Q120, a refractory pulse is generated and the leading edge thereof is coupled back through the reset/inhibit circuit 142 to first turn on transistors Q111 and Q110 to ground base of the voltage doubler pulser transistor Q112 and inhibit the output of any pulse therefrom. Secondly in time, the leading edge of the refractory pulse is coupled back through capacitor C102 to turn on transistor Q108 to effect the resetting of the oscillator circuit to its initial state. The fact that the refractory pulse is made to persist for a substantial period following the reset/inhibit action, renders the circuit insensitive to noise for the duration of the refractory pulse.

A significant feature of the circuit of FIGS. 6a and 6b is that the presence of noise passing through the bandpass amplifier IC1 will cause the circuit to shift to an asynchronous mode of operation whereby the heart will be stimulated by artificial pulses even though normal heart activity is occurring. As was mentioned in connection with the circuit of FIG. 2, this feature is deemed necessary to prevent noise from producing an inhibit/reset function. If the patient should suffer an incidence of heart block while in the presence of external noise, a pacer network without this asynchronous mode of operation would fail to provide artificial stimulating pulses which could result in death.

It is to be recalled that the inhibit/reset circuitry 142 is responsive only to the leading edge of a refractory pulse. In the absence of such a leading edge, the inhibit/reset function will not occur. Referring again to FIG. 7, the first two amplifier input signals appearing at times $t_0$ and $t_1$ represent the normal depolarization pulses produced by the heart. The occurrence of the input at $t_0$ operates in the manner described to produce the refractory pulse on line 140 which persists for a predetermined duration and then reverts back to its quiescent reference value until reinitiated by a subsequent heart pulse at time $t_1$. In the third line of waveforms in FIG. 7 is shown the potential appearing at the base of the transistor Q120 while the bottom-most waveform represents the potential appearing on the base of transistor Q122. It is to be noted that the trailing edge of the refractory pulse on line 140 occurs when the potential on the base of transistor Q122 decays below approximately 0.4 volt, the turn-on threshold of this transistor.

The amplifier input signals appearing at times $t_2$, $t_3$ and $t_4$ represent a spurious input or noise picked up on the implanted electrodes and applied as inputs to the operational amplifier IC1. It is to be noted that these noise pulses are effective to turn on transistors Q120 and Q121 so as to additionally charge capacitor C109 even during a normal refractory period. Because the charging of capacitor C109 prevents the potential on the base of transistor Q122 from decaying to its turn-on threshold, transistor Q122 stays conducting in the presence of noise and hence there is no leading edge transition in the refractory pulse fed back to the reset/inhibit network to occasion the resetting of the oscillator and inhibiting of the output pulse from the voltage doubler pulser in the presence of noise. Since the normal refractory period (without noise) is approximately 300 milliseconds, noise pulses occurring with a period of less than 300 milliseconds, for example, a frequency greater than 4 Hz, will prevent the turn off of transistors Q122 and Q123 so long as the noise pulses fully charge capacitor C109. As the noise frequency increases, it is sufficient that each noise pulse only partially charge capacitor C109. Of course, when the external noise picked up by the heart electrodes ceases to be present, capacitor C109 will discharge through the point where transistor Q122 no longer conducts and the refractory pulse will again revert to its reference state, awaiting the occurrence of the next natural heartbeat.

As was mentioned previously, transistors Q110 and Q111 are used to turn off transistor Q112 and thereby inhibit a pacer output pulse during the reset operation. A normal pacer pulse appearing at the terminals 114 and 120 is capable of passing through the amplifier IC1 and generating a refractory pulse and an undesired inhibit. To avoid this and to insure that a full width pacer pulse will be applied to the heart, the pacer pulse is obtained at point 112 and coupled through a resistor to the base of Q111 to thereby disable transistor Q111 for the duration of the pacer pulse. Thus, the normal inhibit is itself inhibited for the full duration of the pacer output pulse.

The function of the single pole double throw magnetic reed switch 132 is to allow a test to be made on the condition of the power supply battery while the battery remains within the pacer unit implanted in the patient. The reed switch is normally connected as illustrated in FIGS. 6a and 6b such that the junction point 130 is normally connected to ground potential. The reed switch also remains within the pacer unit implanted in the body of the patient. When a permanent magnet is brought into proximity of the reed switch, but outside of the body of the patient, the connection between terminal 133 and ground is broken and at the same time, the resistor R104 is shorted out. Prior to implantation, the resistor R104 is trimmed so that with resistors R103 and R104 in series and with a fresh battery, the oscillator will produce output pulses having a period of approximately 833 milliseconds. Resistor R103 is trimmed so that with resistor R103 included, but with resistor R104 shorted out, the oscillator will have a period of approximately 682 milliseconds. The operation of switch 132 breaks the ground connection at terminal 133 and therefore causes the emitter of transistor Q120 to be tied to the B+ bus through resistors R130, R128, R127 and R126. This insures that transistors Q121, Q122 and Q123 will be held off and the voltage on conductor 140 will be low, disabling the refractory line. As a result, the circuit reverts to the asynchronous mode. Then, if the pulse rate is checked and it is found that the rate at which pacer pulses are produced are less than about 88 beats per minute, the patient or medical technician is made aware that the battery potential is dropping. When the rate during the magnetic test has decreased to approximately 80 beats per minute, the patient should undertake to have the battery replaced.

In a practical embodiment of this invention, the components of the described apparatus of FIGS. 6a and 6b may have the following values:

| | |
|---|---|
| Battery | 2.8 V LiI cell |
| R101 | 51 K |
| R107, 109 | 22 K |
| R108, 111 | 20 K |
| R110 | 30 K |
| R112 | 3 M |
| R113 | 2 M |
| R114 | 1 K |

-continued

| | |
|---|---|
| R115 | 1.2 M |
| R116 | 750 K |
| R117, 125, 129, 136 | 5.1 M |
| R118, 120 | 4.7 K |
| R119 | 2 K |
| R121, 122 | 910 K |
| R123 | 27 K |
| R124 | 4.3 M |
| R126 | 2.2 M |
| R127, 132 | 1 M |
| R130 | 100 K |
| R133 | 240 K |
| R134 | 2.7 M |
| R135 | 1.1 M |
| R137 | 10 K |
| R131 trimmed to yield refractory pulse width ≈ 300 ms | |
| R128 trimmed to yeild R-wave sensitivity of 1.5 V | |
| R106 trimmed to yield osc. output pulse width = 1 ms | |
| R105 trimmed to yield pulse rate decrease of 6 bpm between BOL and ERT (Elective Replacement Time) | |
| R103 trimmed to yield oscillator period of 682 ms with R104 shorted | |
| R104 trimmed to yield oscillator period of 833 ms | |
| C101 | .47 uf |
| C100, 102 | 220 pf |
| C103, 106, 110 | 390 pf |
| C104, 105 | .15 uf |
| C107 | .033 uf |
| C108 | .0022 uf |
| C109 | .02 uf |
| Q101, 102, 103, 106, 110, 121, 123, 124 | 2N3799 |
| Q104, 116, 117 | 1N914 |
| Q105, 107, 108, 111, 112, 118, 119, 120, 122, 125 | 2N2484 |
| Q113 | 2N3700 |
| Q115 | 2N2905 |
| Operational amplifier IC1 | Type CA-3078H |

While the invention has been described with reference to the preferred embodiments thereof, it will be understood by those skilled in the art that the foregoing, as well as other changes in form and detail, may be made therein without departing from the spirit and scope of the invention.

We claim:

1. A cardiac pacer circuit of the type including a pulse generator for producing electrical pacer pulses at a fixed rate and duration, electrode means coupled to the output of said pulse generator for applying said pulses to the heart of a patient and for picking up bipolar depolarization signals from said heart upon the normal beating action thereof and first inhibiting means responsive to said depolarization signals for inhibiting the output of said pulse generator upon the occurrence of said depolarization signals, the improvement comprising:
   a. difference amplifier means coupled to said electrode means for amplifying said bipolar depolarization signals;
   b. a bandpass filter network connected to the output of said difference amplifier means for attenuating the frequency components of the amplifier output signals above and below a predetermined frequency band;
   c. converter means connected to receive the output from said bandpass filter network for converting said bipolar signals to unipolar triggering pulses when the bipolar signals from said filter means exceed a predetermined amplitude; and
   d. means for applying said triggering pulses to said inhibiting means.

2. The cardiac pacer as in claim 1 wherein said converter means comprises:
   a. first and second semiconductor switching means of the same conductivity type each having an input electrode, an output electrode and a control electrode;

b. means coupling said input electrodes of said first and second semiconductor switching means in common and to a source of direct current potential of a first polarity;

c. means connecting said output electrodes of said first and second semiconductor switching means in common and to a source of direct current potential of a polarity opposite to said first polarity; and d. phase splitter means coupling said control electrodes of said first and second semiconductor switching means to the output of said bandpass filter network.

3. Apparatus as in claim 2 and further including means connected to said first and second semiconductor switching means for setting the conduction threshold thereof.

4. An electronic circuit for a cardiac pacer comprising, in combination:

a. an astable multivibrator for normally generating a series of pulses of predetermined duration at a desired rate, unless reset prior to completion of their generation;

b. electrode means electrically coupled to said astable multivibrator and adapted to be surgically implanted on the heart of a patient;

c. a difference amplifier having first and second input terminals and an output terminal;

d. means connecting said electrode means to said first and second input terminals for amplifying the R-wave signal produced during normal ventricular contractions of the heart of a patient;

e. a bandpass active filter connected to said output terminal of said difference amplifier for attenuating the signals from said amplifier which fall outside of a predetermined frequency band;

f. a level detecting circuit connected to receive the output from said bandpass active filter for generating a trigger pulse when the output from said bandpass active filter exceeds a predetermined threshold;

g. a monostable multivibrator circuit connected to the output of said level detector circuit for producing a pulse of predetermined duration greater than the inherent recovery time of said difference amplifier each time said level detector produces a trigger pulse; and h. means connecting the output of said monostable multivibrator circuit to said astable multivibrator for resetting same to an initial condition each time said monostable multivibrator circuit produces a pulse.

* * * * *

UNITED STATES PATENT OFFICE
CERTIFICATE OF CORRECTION

PATENT NO. : 4,041,953
DATED : August 16, 1977
INVENTOR(S) : Jon A. Anderson and Richard W. Kramp It is certified that error appears in the above-identified patent and that said Letters Patent are hereby corrected as shown below:

Column 5, line 20, "power source of" should read -- power source for --.

Column 11, line 62, "bats" should read -- beats --.

Column 12, line 53, "resetinhibit" should read -- reset-inhibit --.  Line 61, change "conconductive" to read -- nonconductive --.

Column 16, line 53, "FIGS. 6a and 6b" should read -- FIGS. 2a and 2b --.

Signed and Sealed this

Fifteenth Day of November 1977

[SEAL]

Attest:

RUTH C. MASON
Attesting Officer

LUTRELLE F. PARKER
Acting Commissioner of Patents and Trademarks